United States Patent [19]
Jennings et al.

[11] 4,376,071
[45] Mar. 8, 1983

[54] MITOGENIC SPINAL CORD GROWTH FACTOR

[75] Inventors: Thomas J. Jennings, Garden City, N.Y.; Allan Lipton, Hershey, Pa.

[73] Assignee: Research Corporation, New York, N.Y.

[21] Appl. No.: 179,945

[22] Filed: Aug. 21, 1980

[51] Int. Cl.³ .............. A01N 63/02; A61K 35/12; C12N 5/00
[52] U.S. Cl. .................. 260/112 R; 424/95; 435/240; 435/241; 435/243
[58] Field of Search ............ 424/84, 12, 1, 95, 85; 260/112 R; 435/240, 241, 243, 7

[56] References Cited
U.S. PATENT DOCUMENTS

| | | | |
|---|---|---|---|
| 4,136,160 | 1/1979 | Cohen | 424/1 |
| 4,230,691 | 10/1980 | Young | 424/85 |
| 4,294,818 | 10/1981 | McMichael et al. | 424/85 X |

OTHER PUBLICATIONS

Jennings et al., Journal of Cell Physiology 100:273-278 (1979).
Wells et al., Chem. Abstracts, vol. 88, 1978, abstract #48443r.
Salafsky et al., Chem. Abstracts, vol. 80, 1974, abstract #68909k.
Weir et al., Chem. Abstracts, vol. 88, 1978, abstract #103132r.

Primary Examiner—Benjamin R. Padgett
Assistant Examiner—M. Moskowitz
Attorney, Agent, or Firm—Oblon, Fisher, Spivak, McClelland & Maier

[57] ABSTRACT

A proteinaceous factor substantially purified from mammalian spinal cord which has mitogenic activity, a molecular weight of about 11,000, a pI of 9.6 and which is heat and acid labile, is useful for the promotion of growth of cells.

13 Claims, 2 Drawing Figures

MITOGENIC SPINAL CORD GROWTH FACTOR

The invention described herein was made in the course of work under a grant or award from the Department of Health and Human Services.

BACKGROUND OF THE INVENTION

1. Field of the Invention

The present invention relates to a mitogenic growth factor from spinal cord, its purification and uses.

2. Description of the Prior Art

Over thirty years ago Hoffman (Hoffman, R. S., Growth, 4:361–376 (1940)) and Trowell and Willmer (Trowell, O. A., and Willmer, E. N., Journal of Experimental Biology, 16:60–70 (1939)), found that water soluble extracts of brain and spinal tissue caused stimulation of cultured chicken fibroblast cells. Twenty-five years later, activity called fibroblast growth factor (FGF) was purified from the brain and pituitary gland (Gospodarowicz, D., Journal of Biological Chemistry, 250:2515–2520 (1975)). The brain factor has been isolated as two basic polypeptides of molecular weights 13,000 (FGF-1) and 11,700 (FGF-2), and the pituitary factor as a basic polypeptide of molecular weight 13,400 (Gospodarowicz et al, ADV. in Met. Disorders, 8:302–335 (1975), Gospodarowicz and Moran, Proceedings of the National Academy of Sciences, USA 71:4584–4588 (1974), Gospodarowicz et al., Journal of Biological Chemistry, 253:3736–3743 (1978), Gospodarowicz et al. "Molecular Control of Proliferation and Cytodifferentiation", Rutter, D., and Papaconstantinou, D. eds., Academy Press, New York (1978), pages 33–61, and Westall et al., Proceedings of the National Academy of Sciences USA, 75:4675–4678 (1978)).

It is believed that amphibian limbs regenerate because their neurons produce a trophic substance that enables the cells at the stump tip to divide (Singer, M., Quarterly Review of Biology, 27:169–200 (1952)). If the amputated limb is denervated early enough, then the regeneration does not occur. Both sensory and motor neurons possess the ability to cause regeneration. However, some regenerative growth can be induced if central nervous tissue homogenates are injected into a denervated limb. It has recently been shown that a basic protein is responsible for this activity (Singer et al., Journal of Experimental Zoology, 196:131–150 (1976)). It has also been found that injections of FGF caused some growth in amputated frog limbs (Gospodarowicz et al., Advances in Met. Disorders, 8:302–335 (1975)), which do not normally regenerate.

Other observations derived from amphibian limb regeneration suggest that the dividing cells might have a capacity to produce a growth self-stimulatory substance that normally resides in nervous tissue.

The availability of nervous tissue—derived purified growth factor is of interest as it would be a selective marker for nervous tissue, and would enable the promotion of growth of various cell lines including but not exclusively, transformed cell lines.

SUMMARY OF THE INVENTION

Accordingly, one object of the invention is to provide a nervous tissue—derived purified growth factor.

Another object of the invention is to provide a process for the purification of a growth factor from nervous tissue, specifically from spinal cord.

Yet another object of the invention is to provide a method for the promotion of growth in animal cells by adding thereto a purified growth factor isolated from spinal cord.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

The present invention provides a growth factor (mitogenic factor) from nervous tissue, specifically from spinal cord tissue. The spinal cord growth factor ("SCGF") has a molecular weight of about 11,000, a pI of 9.6 as determined by isoelectric focusing, is inactivated by extremely acid or basic conditions (pH 2 or 11), is heat labile (inactivation beyond 60° C. for about 20 minutes or more), and has mitogenic activity which is at least partially sensitive to trypsin. This indicates that the factor is at least partly protein. The factor does not contain any or negligible amounts of hexose sugars.

The growth factor is purified from spinal cords. The mitogenic activity is not species specific and can be isolated from mammals, such as rats, mice, bovids, humans and the like. It is preferred to isolate it from bovine spinal cord, more preferably neonatal spinal cords. Spinal cords are homogenized and extracted in buffer. Buffers capable of maintaining a pH around neutrality, i.e., 6.5–8.5, can be used. Such buffers include but are not limited to phosphate, tris hydroxymethylaminomethane ("Tris"), HEPES, glycine, imidazole, and the like. Concentration of the buffer may range from 0.001 M to 1.0 M, preferably around 0.01 M. The time of extraction varies between a few minutes up to a few hours, and can be readily ascertained by visual observation of the homogenate of the final suspension. The temperature ranges from 0° C. to about 40° C. The extraction and preparation of the homogenate can normally be carried out using a mechanical blender or tissue homogenizer or sonicator.

Figure 1:
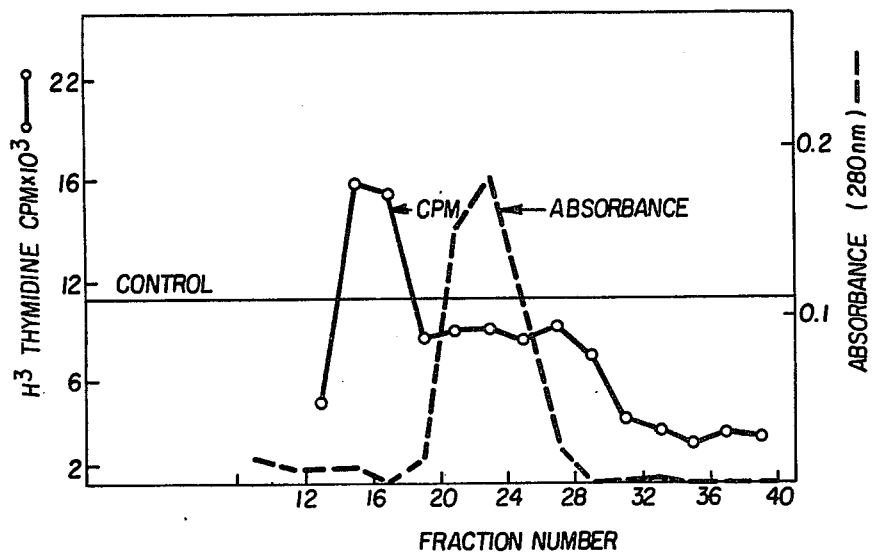
FIG. 1 shows a column chromatography of bovine spinal cord on dextran which is cross linked with epichlorohydrin, having a fractionation range for peptides and globular proteins of 4,000–150,000 (G-100 Sephadex ®). A two ml sample of the active fraction from the filter residue of an ultrafilter which excludes molecules greater than 15,000 daltons was placed on a 2.5 cm X30 cm G-100 Sephadex column using pH 7.4 0.01 M tris buffer; 5-milliliter samples were collected and assayed.
Figure 2:
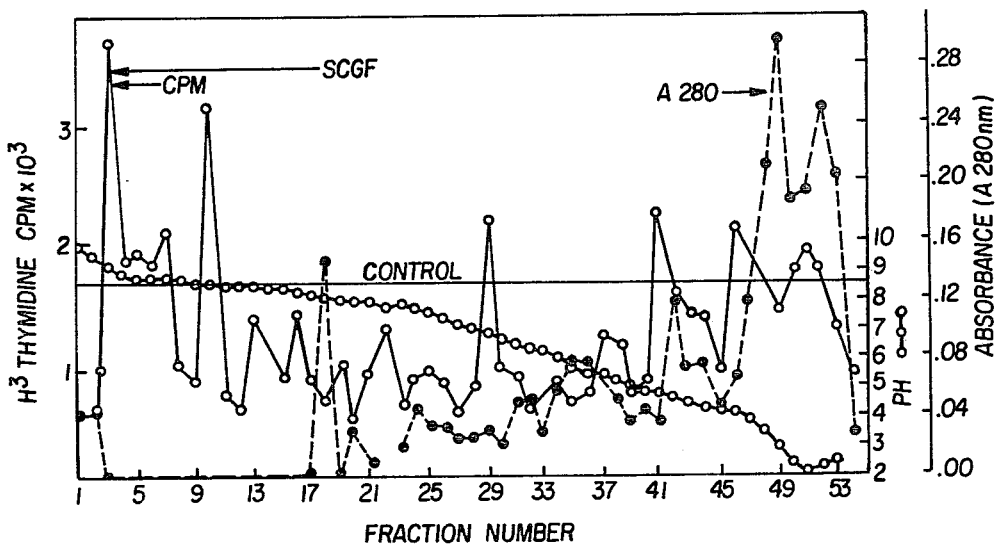
FIG. 2 shows the isoelectric focusing of bovine spinal cord growth factor. For details, see Materials and Methods.

The homogenate suspension is separated into a solid phase and a liquid phase by standard biochemical separation methods such as centrifugation or filtration. The spinal cord growth factor is present in the liquid supernatant or filtrate. The solid residue is discarded. After separation of the residue, the liquid fraction is fractionated using fractionation means capable of separating molecules according to their molecular size. These methods are well known to those skilled in biochemistry and include, but are not limited to ultrafiltration and gel permeation chromatography. Using one or more of such methodologies, a fraction is ultimately separated which comprises the molecular weight range of 10,000–15,000 daltons. Preferably, one or more ultrafiltration steps are first carried out using a commercially available ultrafiltering device. For example in a first step, an ultrafilter is used which excludes molecules greater than 30,000 daltons. The filtrate liquids, which contain the desired fraction of 10,000–15,000 daltons, is refiltered using an ultrafilter which excludes molecules greater than 1,500 daltons. The residue from this ultrafiltration system contains molecules in the range of 1,500–30,000 daltons, and therefore includes the desired fractionation range. The desired range is then further narrowed by means of chromatography on dextran cross-linked with epichlorohydrin ("Sephadex ®"). This chromatographic method utilizes the principle of gel filtration and is well known to those skilled in the art. Preferably, a highly cross-linked dextran is used, most preferably one having fractionation range for peptides and globular proteins in the range of 4,000–150,000 (Sephadex G-100). Such a fractionation on Sephadex G-100 is shown in FIG. 1. The above mentioned buffers, pH's ranges, concentrations and temperatures can be used. The search and isolation of mitogenic activity from the fractionation procedures can be carried out using an assay system of $H^3$ thymidine as described infra, in the Experimental Section.

If necessary, the overall purification can be further increased by isoelectric focusing chromatography, a technique which also serves to characterize the pI of the material, as being in the range of 9.5–9.8. Isoelectric focusing is carried out over the range of pH 3.5–10.0 and serves to separate molecules on the basis of their overall charge in relation to the pH of the medium. Well known desalting techniques can be used thereafter.

An overall purification of between 2,000 and 3,500 increase in specific mitogenic activity over the spinal cord homogenate, can be obtained using these procedures. The final product is pure and homogeneous by SDS polyacrylamide gel electrophoresis.

The growth factor of the invention can be used as a mitogenic factor for both normal and transformed cells. It promotes the growth of animal cell lines in vitro. Examples of such cell lines are mammalian cell lines, such as rat cells, mice cells and human cells. As such, it finds utility as a purified nutrient factor for the growth of cell lines used in the screening of chemotherapeutic agents.

Another utility for this factor is in the preparation of antibodies against it. Protein hormones, such as SCGF, work on the cell at a cell membrane receptor site. Binding of the factor to the site stimulates cell growth. Antibodies to SCGF will, by complexing with free or cell-bound SCGF, interfere with cell growth stimulation. When antibody-SCGF complex is bound on the cell membrane, the cell will be attacked by complement and lymphocytes, causing cell destruction. Antibodies such as IgG, IgA, IgM, IgE from any antibody - producing source, e.g. horses, goats, rabbits, humans and the like, can be used. Hybridoma antibodies can also be used. Antibodies can be provided parenterally (intramuscularly, intravenously, intraperitoneally, subcutaneously) to the animal with the tumor.

The growth factor can also be used as a diagnostic marker for neurological disease and spinal cord or nerve damage. By measuring is concentration in the blood or body fluids as for by example by radio immunoassay or enzyme immunoassay it may be possible to follow the course of a variety of neurologic diseases such as multiple sclerosis. It has been observed that lymphocytes from patients with multiple sclerosis (M.S.) are sensitized to myelin basic protein (a protein capable of producing experimental allergic encephalitis and thought to be the focal point of the body's autoimmune attack in multiple sclerosis) before the clinical presentation of an M.S. attack. This implies that the CNS is being biochemically damaged before the clinical onset. By detecting a rise in SCGF levels in the blood as an index of CNS damage, it is possible that clinical onset may be prevented. Another possible utility for antibodies to SCGF is in the healing of damaged spinal cord, by preventing the SCGF stimulated formation of interfering glial cell scar tissue.

Having now generally described this invention the same will be further illustrated by certain specific examples which are included herein for purposes of illustration only and are not intended to be limiting thereof.

MATERIALS AND METHODS

Swiss 3T3 and SV3T3 cells were routinely cultured in Dulbecco and Vogt's modification of Eagle's medium in the presence of 10% FCS (fetal calf serum). The cells were transferred with the use of calcium and magnesium free 0.3% trypsin solution containing 0.14 M NaCl, 2 mM KCl, 4 mM $Na_2HPO_4$, 4mM $KH_2PO_4$, and 5 mM dextrose. After centrifugation, the cells were washed twice in medium and placed at the appropriate density in 60 mm plastic dishes.

ASSAY FOR MITOGENIC ACTIVITY

Fifty-thousand 3T3 cells were plated in 10% calf serum in 0.1 ml of Dulbecco's medium, which was removed after eight hours and replaced with 1% calf serum in Dulbecco's medium. The cells were incubated in a 12% $CO_2$ atmosphere at 37° C. Then after 24 hours the medium was again replaced with 1% calf serum in Dulbecco's medium and then 0.05-ml samples to be tested were added to the wells. Sixteen hours later, 0.05 microcuries of $^3H$ was put into each well and 11 hours after this the cells were harvested with a cell harvester. The DNA was precipitated on filters with 5% trichloroacetic acid and the radioactivity was counted on a scintillation counter. The data is presented in cpm.

PURIFICATION OF SPINAL CORD GROWTH FACTOR

Two neonatal bovine spinal cords were homogenized in 250 ml of pH 7.4, 0.01 M Tris solution using a blender. The homogenate was centrifuged twice at 25,000 g for one-half periods. The supernatant was then placed on an Amicon filtering system using a PM 30 filter (filter excludes molecules greater than 30,000 daltons). Then the filtrate was placed again in the Amicon filtering system this time with a UM2 filter (excluding molecules greater than 1,500–30,000 daltons) and was next chromatographed on a 2.5×30 cm Sephadex G-100 column using a pH 7.4, 0.01 M Tris buffer. Five-milliliter samples were collected. Fractions containing mitogenic activity were then placed on a 110 ml LKB isoelectric-focusing unit using a pH 3.5–10.0 ampholines. The voltage was 1,500 volts and a constant power of 5 watts was applied for 24 hours. The activity occurring around pH 9.5–9.8, was collected and desalted by dialysis for two days against distilled water and acid.

Homogeneity was established by sodium dodecyl sulfate polyacrylamide gel electrophoresis.

Table 1 demonstrates the recovery of spinal cord growth factor:

TABLE 1

| Fraction | Total protein (mgm) | Total Units[1] | Specific activity (units/mgm) | Overall Purification | % recovery |
|---|---|---|---|---|---|
| Spinal cord homogenate | 1 × 10⁶ | 15.5 × 10⁶ | 15.5 | 1.0 | 100% |
| UM2 filtrate | 1.1 × 10⁴ | 5.2 × 10⁵ | 47 | 3.0 | 3% |
| Sephadex G-100 | 1.8 | 6.2 × 10⁴ | 34,000 | 2,190 | 0.36% |
| Isoelectric focusing | 0.18 | 9.6 × 10³ | 53,020 | 3,420 | 0.056% |

[1] 1 unit of activity = The sample to be tested gives twice the cpm of $^3$H—thymidine incorporation as does a control plate (no additions).

i.e., $\frac{\text{cpm }^2\text{H—thymidine incorporation of sample to be tested}}{\text{cpm }^2\text{H—thymidine incorporation control plates}} = 2$

TABLE 2

Table 2 compares the properties of the growth factor of the invention with central nervous system factors isolated in the prior art:

| | Mol. Wt. | p$^I$ | Heat | Acid | Trypsin | Sugar content | 3T3 cells |
|---|---|---|---|---|---|---|---|
| Bovine Pituitary FGF | 13,400 | 9.6 | Labile | Labile | Sensitive | Negligible | + |
| Bovine brain FGF-1 | 13,000 | 9.6 | Labile | Labile | Sensitive | Negligible | + |
| FGF-2 | 11,700 | 9.6 | Labile | Labile | Sensitive | Negligible | + |
| Bovine Spinal cord (SCGF) | 11,000 | 9.6 | Labile | Labile | Sensitive | Negligible | + |

The differences between SCGF and FGF can also be ascertained by comparative SDS gel electrophoresis which demonstrates that the band for the growth factor from spinal cord does not run at the same point as the band for pituitary FGF.

MITOGENIC ACTIVITY OF THE SPINAL GROWTH FACTOR.

Active fractions from the Sephadex G-100 were tested to demonstrate that they caused transformed SV3T3 cells to multiply; 1×10⁵ cells were plated in 5 ml Dulbecco's medium with 0.2% fetal calf serum. The cells were allowed to attach and then samples were added the same day. On day 4, the cells were removed with trypsin and counted using a counter. SV40 3T3 cells are definitely simulated to multiply (see table 3). Pituitary FGF on the other hand does not stimulate the multiplication of SV3T3 cells.

TABLE 3

The effect of the active column fractions on SV40 3T3 cell multiplication

| Volume added | Protein added (gm/ml) | SV3T3 cells number (× 10⁵) |
|---|---|---|
| Control | — | 1.38 |
| 0.1 ml | 0.6 | 1.77 |
| 0.25 ml | 1.25 | 2.22 |
| 0.5 ml | 3.0 | 2.06 |

Tubes 15–17 from the Sephadex G-100 columns were used.

Having now fully describes this invention it will be fully apparent to one of skill of the art that many changes and modifications can be made thereto without departing from the spirit or scope of the invention set forth herein.

What is claimed as new and intended to be covered by Letters Patent is:

1. A substantially purified proteinaceous factor obtained from spinal cord which has mitogenic activity, a molecular weight of about 11,000, a pI of 9.6 and which is heat and acid labile.

2. The factor of claim 1 which is from mammalian spinal cord.

3. The factor of claim 2 wherein said mammal is a bovid.

4. The factor of claim 1 which has mitogenic activity towards transformed animal cells.

5. A process of purifying a mitogenic factor from mammalian spinal cord which comprises:
   homogenizing mammalian spinal cord; separating said homogenate into a solids fraction and a liquid fraction;
   fractionating from said liquid fraction molecules which lie in the range of molecular weights 10,000–15,000.

6. The process of claim 5 which after said fractionation step further comprises isolating a proteinaceous mitogenic factor having a molecular weight of about 11,000 and a pI of 9.6.

7. The process of claim 5 wherein said separation step is carried out by centrifugation.

8. The process of claim 5 wherein said fractionation step comprises
   ultrafiltering said liquid fraction, thereby obtaining a residue, and chromatographing said residue on dextran beads crosslinked with epichlorohydrin.

9. The process of claim 6 wherein said isolation step of said factor is carried out by isoelectric focusing.

10. A method of promoting the growth of animal of cells which comprises: contacting said cells with the factor of claim 1.

11. The method of claim 10 wherein said cells are transformed cells.

12. The method of claim 10 wherein said animal cells are mammalian cells.

13. A method of preventing the growth of transformed cells which comprises:
   allowing said transformed cells to bind to a complex of the spinal cord growth factor of claim 1 and an antibody thereto in the presence of complement; thereby causing the complement mediated lysis of said transformed cells.

* * * * *